United States Patent [19]

Williamson

[11] 4,164,137

[45] Aug. 14, 1979

[54] METHOD OF MEASURING VOLUME OF AIR ENTRAINED IN HYDRAULIC FLUIDS

[75] Inventor: William A. Williamson, Niles, Mich.

[73] Assignee: Clark Equipment Company, Buchanan, Mich.

[21] Appl. No.: 911,730

[22] Filed: Jun. 2, 1978

[51] Int. Cl.² .............................................. G01N 7/00
[52] U.S. Cl. ...................................................... 73/19
[58] Field of Search ................ 73/19, 61 R, 61.4, 61.2

[56] References Cited

U.S. PATENT DOCUMENTS

| 3,731,530 | 5/1973 | Tanguy et al. | 73/61 R |
| 3,952,580 | 4/1976 | Bennett | 73/61.4 |

OTHER PUBLICATIONS

Honeyman et al., "Air in Oil-Available Measurement Methods", The BFPR Journal, 1978, 11, 3, pp. 275-281.

Primary Examiner—Stephen A. Kreitman
Attorney, Agent, or Firm—J. C. Wiessler

[57] ABSTRACT

A method for measuring the volume of air entrained in hydraulic fluid by using improved apparatus for measuring separately the particle contamination count in the fluid and the air bubble entrainment plus the particle contamination count, the difference of which equals the air entrainment count from which the volume of air entrained is determinable.

6 Claims, 2 Drawing Figures

METHOD OF MEASURING VOLUME OF AIR ENTRAINED IN HYDRAULIC FLUIDS

BACKGROUND OF THE INVENTION

Control and knowledge of the amount of contamination in hydraulic fluids utilized in such things as industrial, vehicular and machine hydraulic systems is of importance, and often of critical importance, to the proper functioning of the system and components therein. In addition to the problem of particulate contamination is the adverse effect resulting from the presence of air in the system fluid of high pressure hydraulic systems in particular. The detrimental effects of high air ratio levels are well-known, and include sluggish response, noisy operation, loss of power, pump cavitation, decreased component life, and erroneous performance evaluations. No prior art means is known for measuring air-liquid volume ratios because of the difficulty of measuring the volume of air in hydraulic fluid under different operating conditions. Without some means of assessing air-liquid volume ratios it is difficult to establish an acceptable air ratio level ralative to system performance and component lift.

In carrying out the method of this invention I utilize the improved apparatus of my co-pending application Ser. No. 899,662, entitled "Apparatus For Counting Particle Contamination Of Liquid," filed Apr. 24, 1978.

Various methods for measuring air in hydraulic fluid are discussed in "The BFPR JOURNAL", 1978, 11, 3, 275–281, in an article entitled "Air In Oil-Available Measurement Methods." Also, U.S. Pat. No. 3,952,580, granted Apr. 27, 1976, represents known prior art for counting particulate contamination in a liquid.

As is well-known, entrained air is in the form of discreet bubbles which are held in the body of a fluid whereas dissolved air is in solution with the fluid. For any given hydraulic fluid under any operating conditions my improved method can be utilized to accurately determine the entrained air-liquid volume ratio.

SUMMARY

My invention comprises an improved method for measuring both particulate contamination and entrained air in hydraulic fluid by counting the total of air entrained in the form of bubbles and particulate matter, and capable of also counting particulate matter only, whereby the difference equates to the total air entrained from which the entrained air-liquid volume ratio under any given system operating conditions is determinable.

It is a primary object of the invention to provide an improved method for determining the volume of air entrained in hydraulic fluid.

Another object is to utilize improved apparatus in carrying out the above method.

DETAILED DESCRIPTION

Figure 1:
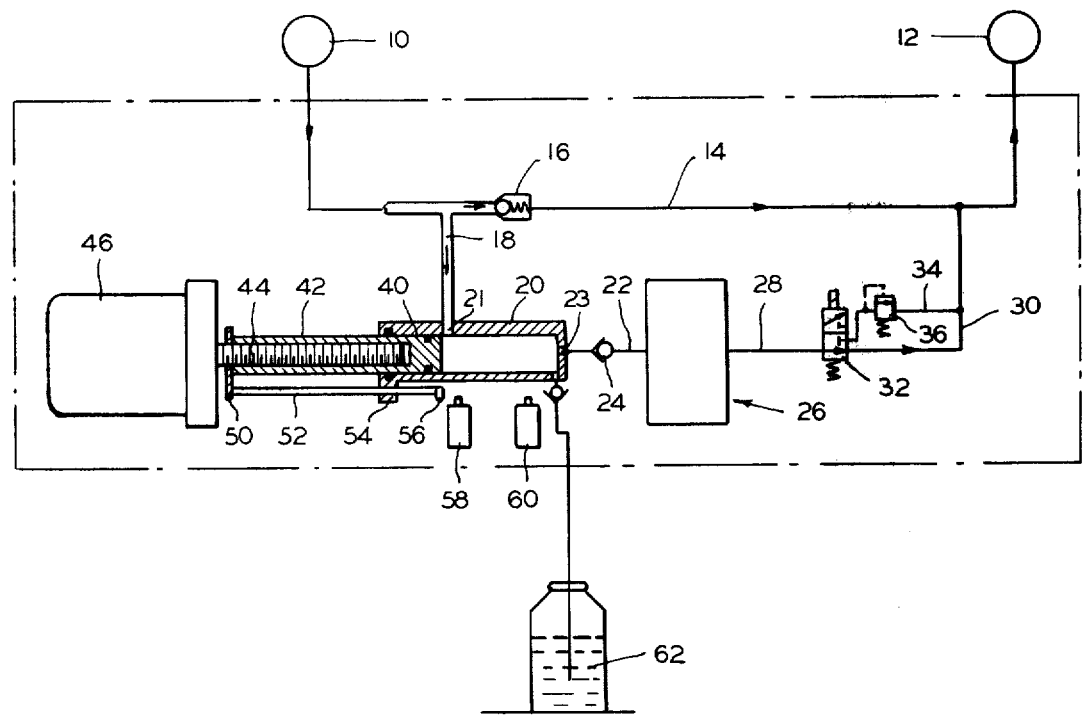
FIG. 1 is a schematic view of apparatus which may be utilized in carrying out my invention.

Referring to FIG. 1, the operation of the apparatus shown for counting foreign matter in a hydraulic system will first be described with respect to the counting of particulate contamination. First, it should be understood that commercial particle counters, represented at numeral 26 in FIG. 1, cannot discriminate between particulate contaminants and entrained air bubbles, and counts both. The hydraulic oil to be sampled is represented as flowing from a source 10 to a location 12 by way of a conduit 14 in which is located a check valve 16 which provides back pressure and permits hydraulic oil to flow through a conduit 18 into a cylinder 20. The liquid then flows through conduit 22 having therein a check valve 24 and through the sensor of a particle counter represented diagrammatically at 26, from whence it flows back into conduit 14 by way of either conduits 28, 30 and one side of a double acting solenoid operated valve 32, or by way of conduits 28, 34 and 30 and the opposite side of valve 32 and a high pressure relief valve 36. Particle counter and sensor unit 26 may be Model No. 345 manufactured by Royco Instruments, Inc. of Menlo Park, Calif. It is important to note that the flow through on-line conduit means which parallels conduit 14 of the main hydraulic system includes cylinder 20 and spaced ports 21 and 23 thereof as a part of said conduit means. Further discussion concerning the cylinder 20 as being a part of the said conduit means, which includes conduits 18, 22, 28, 30 and 34, will appear below.

A piston 40 is located in cylinder 20 shown in retracted position. It has an elongated cup-shaped portion 42 which is internally threaded and which extends outwardly of the cylinder for connection with a rotatable screw 44 adapted to be operated by a low horsepower constant speed gear motor 46. As the gear motor is rotated the rotational movement is converted to linear movement at piston 40.

At the one end of piston 40 is secured a lug 50 to which is fixed a rod 52 which passes through an opening in a lug 54 on the one end of cylinder 20. A probe 56 is connected to the end of rod 52. Lug 54 and stem 52 prohibit rotational movement of piston 40 during linear movement thereof in cylinder 20. Probe 56 is adapted to operate switch assemblies 58 and 60 during forward movement of the piston which starts and stops the counter 26.

In normal operation part of the oil traveling from source 10 to point 12 is forced by check valve 16 to pass through the on-line by-pass sampling circuit in a continuous flow of oil. When the operator of the machine or other apparatus to the hydraulic system of which my invention is connected desires to take a sample, gear motor 44, 46 is energized which starts piston 40 moving forwardly in cylinder 20. The initial portion of piston movement seals conduit 18 from the cylinder so that no additional oil can enter the sampling circuit, at which time there is a fixed volume of oil trapped within the sampling circuit. The control of the gear motor may be normally connected so that solenoid valve 32 is actuated when the motor is energized to connect conduits 28 and 30 by way of pressure relief valve 36 and line 34.

Continued movement of piston 40 causes probe 56 to trip switch 58 which starts the operation of particle counter 26 which continues until the piston moves to such a position that probe 56 trips switch 60 stopping counter 26. It will be appreciated by persons skilled in the art that additional switches can be incorporated to de-energize the gear motor, reset the counter, reverse the motor in order to return piston 40 to its illustrated position, and to de-energize solenoid valve 32 to return it to its illustrated position.

As will now be apparent, the rate of flow through counter 26 can be precisely controlled by a selected combination of motor speed and piston size, a fixed volume being always delivered to the counter during the particle contamination count irrespective of oil viscosity as controlled by the selected positions of control switches 58 and 60. With oil under relatively high pressure, preferably about 1500 psi as controlled by valve 36, it will be seen that air bubbles entrained in the oil are either driven into solution or compressed to such a small size that they will not be counted by the particle counter.

To take a particle count the operator need only hook up two quick disconnects, not shown, between the sampler circuit conduits 18, 30 and the main system conduit 14, start the prime mover, pump or other source pressure apparatus in the hydraulic system being sampled, and start gear motor 46. The remainder of the operation is automatic with the sampler device starting and stopping counter 26 at the correct times; the device is reset by running motor 46 in reverse following each sampling operation. A container 62 is illustrated to provide a source of oil fill for the cylinder during retraction of the piston preparatory to taking the next sample.

In order now to determine the total count of particulate matter plus entrained air bubbles it is merely necessary to run a sample as above described following actuation of a control switch, not shown, to deactivate solenoid valve 32 so that during operation of the gear motor to drive piston 40 forwardly in cylinder 20 the sample liquid flows through counter 26 to a location 12, such as a reservoir, at reservoir pressure, as shown, or at any selected low pressure for which valve 32 may be designed so that the air in the hydraulic fluid is entrained in bubble form, and not dissolved as when relatively high back pressure is generated by the activation of solenoid valve 32. Thus, counter 26 counts the total of particulate matter and air entrained as bubbles. Inasmuch as such particle counters as above identified are capable of discriminating the size of the air bubble sphere, as 10, 30 or 50 microns in diameter, for example, it will be apparent that the total volume of air entrained is determinable simply by subtracting from the total count the count of the particulate matter and multiplying the difference by the bubble volume. It will further be understood that the condition of the hydraulic fluid can be determined under any existing conditions of operation, the volume of entrained air varying with changes in certain system operating conditions, system air-ingression rate, and for other reasons, as is known.

Figure 2:
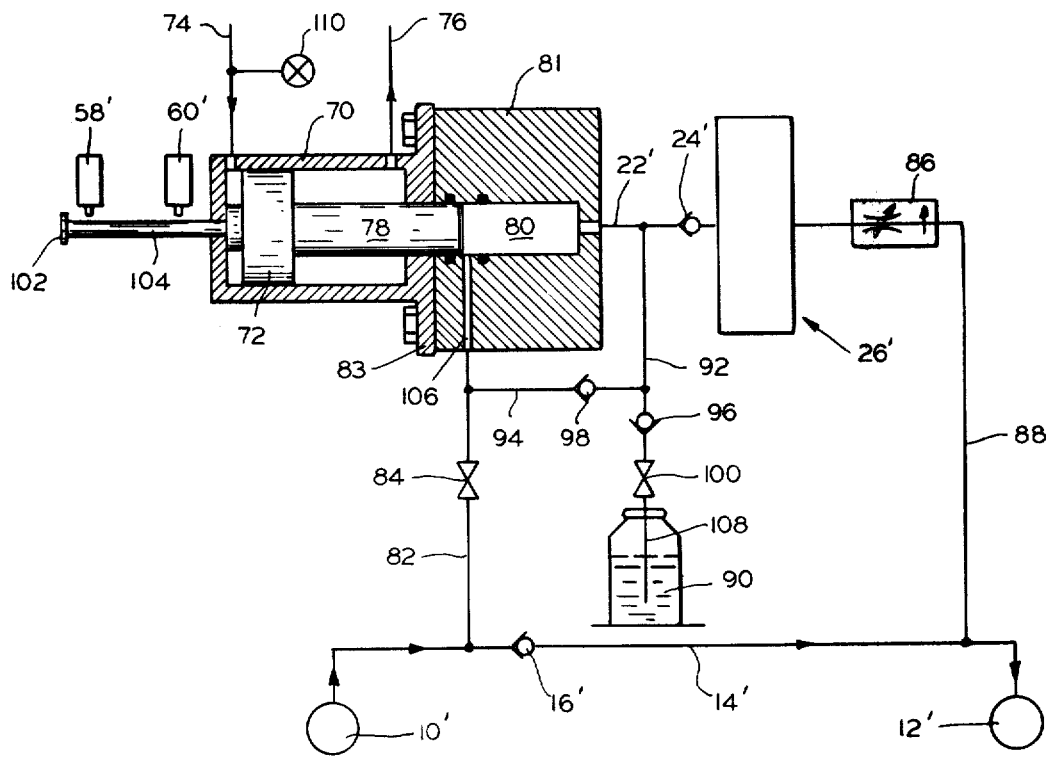
FIG. 2 is a schematic view of a second and preferred embodiment of such apparatus.

In the embodiment of apparatus used in carrying out the method as shown in FIG. 2, similar elements have been similarly numbered but carry a prime designation. An air cylinder and piston 70, 72 replaces the gear motor and screw arrangement of FIG. 1, the piston being driven in a forward direction by air pressure supplied by conduit 74 and in a reverse direction by air pressure supplied by conduit 76. A connected hydraulic piston 78 is operable in a cylinder 80 which is formed in a housing 81 and a bolted on cover 83 of cylinder 70, the by-pass sampling circuit comprising conduit 82 having a manual valve 84 entering one end of cylinder 80, and conduit 22' connected from the remote end of the cylinder to conduit 14' by way of check valve 24', counter 26' and a pressure compensated flow control valve 86 in a conduit 88. A container or bottle sampler 90 is connected to conduits 22' and 82 by way of conduits 92 and 94, check valves 96 and 98, and a manual valve 100.

Switch assemblies 58' and 60' are operated as in FIG. 1 by a probe 102 connected to the outer end of a stem 104 which projects outwardly of the base end of cylinder 70 and which is connected to the one end of piston 72. Operation of piston 72 forwardly causes, when operated on-line, a sample of oil to be trapped in cylinder 80 which upon inward movement of piston 78 opens check valve 24' while holding closed check valves 96 and 98 and discharging through particle counter 26' a predetermined volume of oil at a predetermined pressure as determined by the operation of switches 58' and 60', as previously explained, and by the operation of pressure compensated flow control valve 86. The latter valve is designed to permit a precise amount of oil to flow irrespective of variations of pressure existing upstream of the valve. Thus, valve 86 permits oil to flow through the by-pass sampling circuit so that the oil in cylinder 80 always is representative of the contamination level in the hydraulic system. Use of other types of flow control valves adjustable to deliver desired oil flow under high pressure conditions result in little or no flow through the valve when a particle count of a sample is not being taken, whereby sample oil is not necessarily representative of the oil condition of the system. Valves of the type illustrated schematically at 86 are manufactured by Fluid Controls of Mentor, Ohio.

Again, the particle counter is turned on and off and reset by switches 58' and 60' and, as will be appreciated, knob 102 may be adapted to also actuate switches for controlling air flow into conduits 74 or 76 for automatic cycling of the air cylinder.

It will be appreciated that with high air pressure input to the air cylinder from conduit 74 an accurate count of particulate matter occurs, the same as in FIG. 1 when solenoid valve 32 is activated. One the other hand, a low air pressure input, such as 5 or 10 psi, as may be controlled as shown schematically by a manually adjustable air bleed-off valve 110, effects a total count of particulate matter plus entrained air bubbles at counter 26'. As before, the difference in counts can be translated into entrained air volume or air-liquid volume ratio under any given operating conditions.

Of course, as many samples as may be thought necessary under any given conditions of operation in the use of either embodiments of FIGS. 1 or 2 should be taken to determine whether and to what extent the average air entrainment may vary from that of any given sample.

As will be apparent, on the return stroke of piston 78 oil is drawn from conduit 14' by way of conduits 82, 94, 92 into cylinder 80 through open manual valve 84 and check valve 98. When the piston has completed its retraction oil is available to the cylinder by way of conduits 82 and 106. Shut-off valves 84 and 100 are used to shift the sampling operation between the on-line mode and the bottle sampling mode. In the on-line mode valve 84 is open and valve 100 is closed, whereas in the bottle sampling mode valve 84 will be closed and valve 100 open. When a bottle sample is desired line 108 is lowered into container 90 and piston 78 started from its extended position into cylinder 80. As the piston 78 is retracted by piston 72 through the application of air pressure into conduit 76 oil is drawn through the valves 100, 96 and conduits 108, 92 and 22' into cylinder 80 which, when the piston is fully retracted is full of oil. The piston is then actuated forwardly in cylinder 80 and the particle count or air entrainment plus particle count of the bottle sample taken as described above relative to on-line sampling. It will be noted that cylinder 80 forms a part of the by-pass conduit means the same as in FIG. 1 and for the same advantageous purpose.

The embodiment of FIG. 2 is preferred to that of FIG. 1 primarily because of the availability of standardized and simpler parts to manufacture or procure, and because the use of pressure compensated valve 86 permits the use of the system with a variety of particle counters and with various flow rates, the required adjustment being merely to adjust the desired control pressure at the pressure compensator valve and the air pressure to the air cylinder. In the FIG. 1 embodiment, on the other hand, such variations require a change in the linear rate of advance of the screw 44 and/or the speed of motor 46.

It will be apparent that if desired a given sample of liquid, such as may be contained in bottle 62 or 90, may be recircuited into the respective bottle so that the same specific liquid sample may be rerun through the counter for measurement of entrained air and particulate matter as above described.

It will be apparent to those skilled in the art that various changes in the sequence of steps of the method and in the structure and relative arrangement of parts may be made without necessarily departing from the scope of my invention.

I claim:

1. A method of counting entrained air bubbles in a liquid comprising the steps of discharging through a particle counter a measured liquid sample at a pressure which dissolves the air bubbles in the liquid or so reduces the size thereof that the counter substantially counts particulate matter only, discharging through said particle counter the same or a second liquid sample of substantially equal measured volume at a pressure which permits the air entrained to form bubbles discernible for counting by the counter, and subtracting from the total count of particles and air bubbles a count of particles.

2. A method as claimed in claim 1 wherein apparatus for counting said air bubbles is connected to a hydraulic system at spaced locations for bypassing a portion thereof, the method including the step of taking random successive measured liquid samples from the hydraulic system whereby to enable on-line sampling while the hydraulic system is in operation.

3. A method as claimed in claim 2 wherein the apparatus includes a conduit bypassing said portion of the hydraulic system in which is located the particle counter and a cylinder-piston means forming a part of the bypass conduit through which is adapted to flow liquid from the hydraulic system, the method including the steps of starting and stopping the particle counter during movement of the piston in the cylinder between predetermined locations therein during which the hydraulic system liquid flow into the cylinder is interrupted to establish the volume of each liquid sample during operation of the particle counter.

4. A method as claimed in claim 1 wherein apparatus for counting said air bubbles is connected to a liquid container, the method including the step of taking the same or successive measured liquid samples from the container.

5. A method as claimed in claim 1 including the step of adjusting the pressure at which the liquid sample or samples is discharged through the particle counter.

6. A method as claimed in claim 1 including the steps of determining the entrained air volume by controlling the pressure at which entrained air forms bubbles of a diameter which is approximately discernible by the counter, and multiplying the air bubble volume by the number of air bubbles entrained in the measured liquid sample to establish the air-liquid volume ratio in that sample.

* * * * *